United States Patent
Muir et al.

(10) Patent No.: US 11,376,092 B2
(45) Date of Patent: Jul. 5, 2022

(54) PARALLAX-FREE INDICATOR DEVICES, SYSTEMS, AND METHODS

(71) Applicant: Biomet Manufacturing, LLC, Warsaw, IN (US)

(72) Inventors: Nicholas Muir, Winona Lake, IN (US); Nathan A. Winslow, Warsaw, IN (US); Stephen H. Hoag, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 57 days.

(21) Appl. No.: 16/324,379

(22) PCT Filed: Aug. 31, 2017

(86) PCT No.: PCT/US2017/049594
§ 371 (c)(1),
(2) Date: Feb. 8, 2019

(87) PCT Pub. No.: WO2018/045160
PCT Pub. Date: Mar. 8, 2018

(65) Prior Publication Data
US 2019/0175298 A1    Jun. 13, 2019

Related U.S. Application Data

(60) Provisional application No. 62/382,411, filed on Sep. 1, 2016, provisional application No. 62/381,904, filed on Aug. 31, 2016.

(51) Int. Cl.
*A61B 90/13*   (2016.01)
*A61B 17/15*   (2006.01)
(Continued)

(52) U.S. Cl.
CPC ............. *A61B 90/13* (2016.02); *A61B 17/15* (2013.01); *A61B 17/1778* (2016.11);
(Continued)

(58) Field of Classification Search
CPC ................................ A61B 90/30; A61B 90/13
See application file for complete search history.

(56) References Cited

U.S. PATENT DOCUMENTS

| | | | | |
|---|---|---|---|---|
| 4,247,770 A | * | 1/1981 | Welch | G01V 9/005 250/253 |
| 5,031,203 A | * | 7/1991 | Trecha | A61B 17/1703 128/898 |

(Continued)

FOREIGN PATENT DOCUMENTS

| | | |
|---|---|---|
| GB | 2302492 A | 1/1997 |
| WO | 2015185864 | 12/2015 |

(Continued)

OTHER PUBLICATIONS

"European Application Serial No. 17847541.4, Response to Communication Pursuant to Rules 161(1) and 162 EPC filed Oct. 21, 2019", 8 pages.

(Continued)

*Primary Examiner* — Jan Christopher L Merene
(74) *Attorney, Agent, or Firm* — Schwegman Lundberg & Woessner, P.A.

(57) ABSTRACT

Various parallax-free indicator devices, systems, and methods are disclosed. The indicator device may have a housing defining an aperture and a light source assembly at least partially disposed in the housing. The housing may be selectively securable via a fastener to an instrument in a selected orientation relative to the instrument. The light source assembly may have a light source operably coupled to a power source via a power circuit. The light source may be positioned within the housing to emit through the housing aperture. Upon activation, the light source assembly emits a parallax-free alignment indicator along an alignment axis that may have at least one of a selected angle and a selected (Continued)

displacement relative to a selected reference axis. The alignment indicator may guide a surgical procedure.

10 Claims, 6 Drawing Sheets

(51) Int. Cl.
    *A61B 90/35*      (2016.01)
    *A61B 17/17*      (2006.01)
    *A61F 2/46*      (2006.01)
    *A61B 17/90*      (2006.01)
    *A61B 90/30*      (2016.01)
    *A61B 90/00*      (2016.01)
    *A61B 17/00*      (2006.01)

(52) U.S. Cl.
    CPC ............ *A61B 90/35* (2016.02); *A61F 2/4612* (2013.01); *A61B 17/90* (2021.08); *A61B 2017/00734* (2013.01); *A61B 2090/309* (2016.02); *A61B 2090/3618* (2016.02)

(56) References Cited

U.S. PATENT DOCUMENTS

| | | | | |
|---|---|---|---|---|
| 5,038,155 A * | 8/1991 | Yamagishi | ............... | B41J 2/325 347/198 |
| 5,052,801 A * | 10/1991 | Downes, Jr. | ............... | F41G 1/35 356/153 |
| 5,320,111 A * | 6/1994 | Livingston | ......... | A61B 17/3403 378/206 |
| 5,426,687 A | 6/1995 | Goodall et al. | | |
| 5,606,590 A | 2/1997 | Petersen et al. | | |
| 5,690,107 A * | 11/1997 | Hofmann | ................ | A61B 6/08 378/206 |
| 6,048,345 A * | 4/2000 | Berke | ................ | A61B 17/1624 606/171 |
| 6,344,039 B1 * | 2/2002 | Tang | ........................ | A61F 9/008 359/368 |
| 2002/0166935 A1 * | 11/2002 | Carnevali | ............... | F16M 11/14 248/276.1 |
| 2004/0014010 A1 * | 1/2004 | Swensen | .................... | F41J 5/02 434/21 |
| 2005/0001585 A1 * | 1/2005 | Tashiro | ................. | H01M 10/46 320/107 |
| 2005/0015099 A1 * | 1/2005 | Momoi | ................... | A61B 34/20 606/130 |
| 2006/0229606 A1 * | 10/2006 | Clement | ............. | A61B 17/7037 606/266 |
| 2007/0000139 A1 * | 1/2007 | Chen | ..................... | G01C 15/004 33/286 |
| 2007/0055291 A1 * | 3/2007 | Birkmeyer | ......... | A61B 17/8875 606/130 |
| 2009/0234360 A1 | 9/2009 | Alexander | | |
| 2009/0243327 A1 * | 10/2009 | Koga | ...................... | B60N 2/067 296/65.15 |
| 2010/0087829 A1 * | 4/2010 | Metzger | ............... | A61B 17/154 606/96 |
| 2012/0296401 A1 | 11/2012 | Potts et al. | | |
| 2014/0100620 A1 | 4/2014 | Mullaney | | |
| 2015/0018842 A1 * | 1/2015 | Rahimian | ............... | A61B 34/30 606/130 |
| 2015/0032153 A1 * | 1/2015 | Quadri | ............... | A61B 17/0057 606/215 |
| 2015/0100058 A1 | 4/2015 | Van Der Walt et al. | | |
| 2016/0022374 A1 | 1/2016 | Haider et al. | | |
| 2016/0166333 A1 | 6/2016 | Wang et al. | | |
| 2018/0326507 A1 * | 11/2018 | Halvorsen | .............. | B25J 9/0009 |

FOREIGN PATENT DOCUMENTS

WO    WO-2016066615 A2    5/2016
WO    WO-2018045160 A1    3/2018

OTHER PUBLICATIONS

"International Application Serial No. PCT/US2017/049594, International Search Report dated Nov. 16, 2017", 2 pgs.

"International Application Serial No. PCT/US2017/049594, Written Opinion dated Nov. 16, 2017", 6 pgs.

"European Application Serial No. 17847541.4, Extended European Search Report dated Apr. 2, 2020", 7 pages.

"European Application Serial No. 17847541.4, Response filed Nov. 2, 2020 to Extended European Search Report dated Apr. 2, 2020", 14 pages.

* cited by examiner

PARALLAX-FREE INDICATOR DEVICES, SYSTEMS, AND METHODS

RELATED APPLICATIONS

This application is a U.S. National Stage Application under 35 U.S.C. 371 from International Application Serial No. PCT/US2017/049594, filed on Aug. 31, 2017, and published as WO 2018/045160 A1 on Mar. 8, 2018, which claims the benefit of priority to U.S. Provisional Patent Application Ser. No. 62/382,411, filed Sep. 1, 2016, and U.S. Provisional Patent Application Ser. No. 62/381,904, filed Aug. 31, 2016, the contents of each of which are incorporated herein by reference.

FIELD

The present disclosure relates to parallax-free indicator devices, systems, and methods for use in surgical procedures.

BACKGROUND

This section provides background information related to the present disclosure, which is not necessarily prior art.

Many orthopedic surgical procedures include steps requiring particular orientation of a portion of patient's anatomy with respect to another portion of the patient's anatomy or to a medical device, such as a surgical tool or an implant. One example of such a procedure is shoulder replacement surgery, where accurately determining humeral version is important to achieving an optimal patient outcome. Humeral version can be described as the rotation of the humeral head relative to the epicondylar axis of the elbow. Version rods attached to surgical instruments can be used to aid healthcare providers in visually determining proper orientation of the patient's anatomy. However, despite use of version rods, visually determining orientation, or humeral version, remains prone to inaccuracy due to user-induced error.

SUMMARY

This section provides a general summary of the disclosure, and is not a comprehensive disclosure of its full scope or all of its features.

The present inventors have recognized that visual determination of proper orientation of patient anatomy using version rods is prone to inaccuracy based on a user's position with respect to the version rod and the patient anatomy of interest and, additionally or alternatively, variability of one or more user's position, as such orientation is sought to be maintained or recreated during the course of a procedure. Such inaccuracy is related to "parallax" or a displacement or difference in the apparent position of an object viewed along two different lines of sight. Devices, systems, and methods for accurately determining and maintaining anatomical orientation, regardless of a person's or machine's line of sight, would therefore be desirable. Accordingly, the present teachings provide for parallax-free indicator devices, systems, and methods. The device can comprise a housing and a light source assembly at least partially disposed in the housing. The housing can define an aperture. The housing can be selectively securable via a fastener to an instrument in a selected orientation relative to the instrument. The light source assembly can comprise a light source that can be operably coupled to a power source via a power circuit. The light source can be positioned within the housing to emit through the aperture of the housing. Upon activation, the light source assembly can emit a parallax-free alignment indicator along an alignment axis. The alignment axis can have at least one of a selected angle and a selected displacement relative to a selected reference axis. The alignment indicator can guide a surgical procedure.

The present teachings also provide for methods for accurately determining anatomical orientation and, additionally or alternatively, maintaining or recreating anatomical orientation during the course of a surgical procedure. Such methods can comprise securing a device to a surgical instrument, activating a light source of the device to project an alignment indicator along an alignment axis, aligning an anatomical feature of a patient with the alignment indicator, and fixing the position of at least a portion of a surgical instrument relative to a surgical site on the patient.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present teachings provide for parallax-free indicator devices, systems, and methods. Such devices, systems, and methods can facilitate accurate orientation of patient anatomy regardless of a user's position with respect to the indicator device and the patient anatomy of interest and, additionally or alternatively, regardless of variability of any user's position as such orientation is sought to be maintained or reestablished during the course of a procedure. In one exemplary implementation, the devices, systems, and methods disclosed herein can enable accurate determination and maintenance or reestablishment of humeral version through reaming, rasping, resection, and implant insertion during a shoulder replacement procedure regardless of the position of any user with respect to the indicator device or the patient's forearm.

Figure 1:
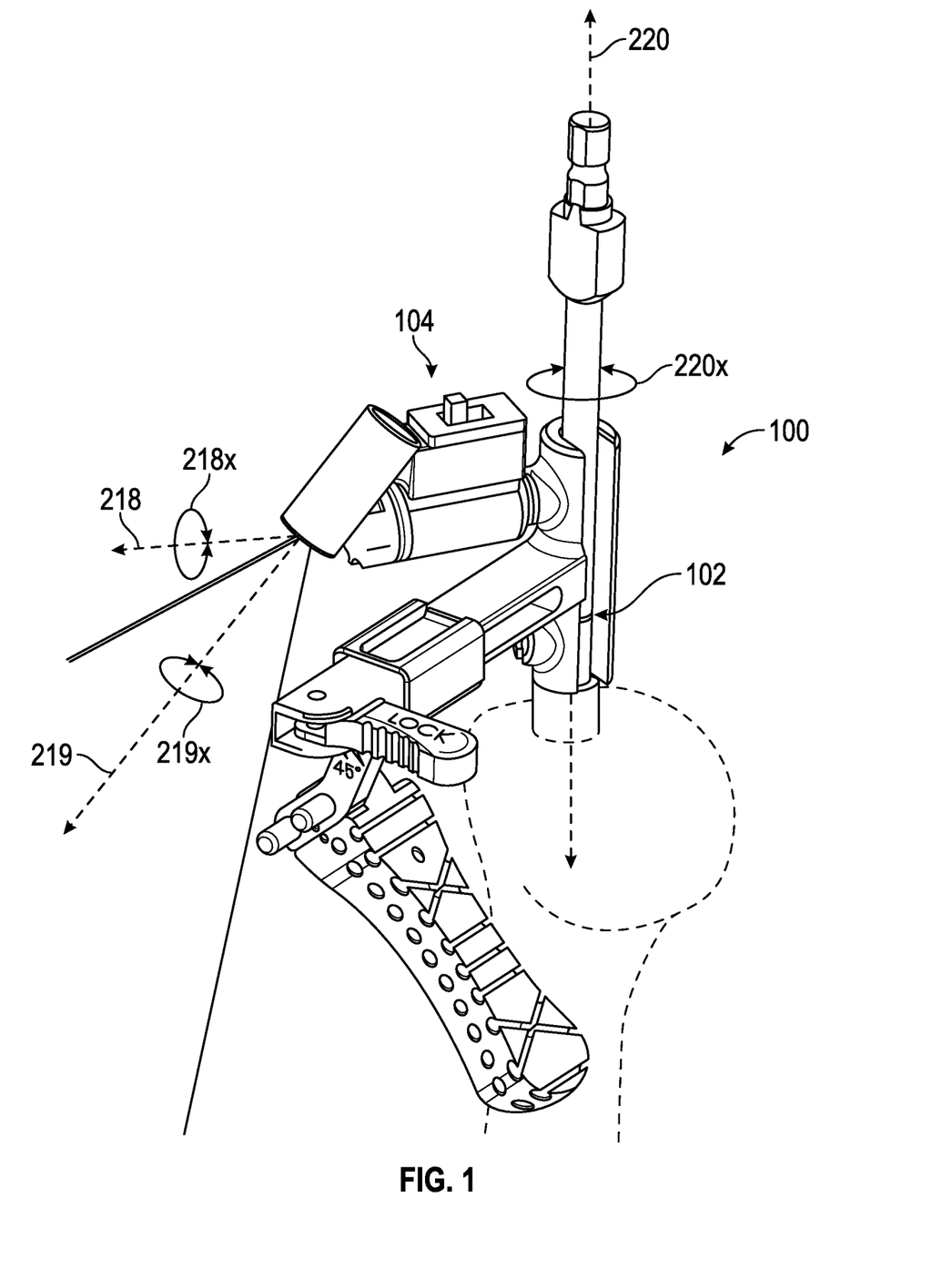
FIG. 1 illustrates an alignment indicator device registered to, or connected to, a surgical instrument that is installed in the humerus, according to an exemplary embodiment of the invention.

With initial reference to FIG. 1, a system 100 comprises a surgical instrument 102 and a parallax-free alignment indicator 104. In one aspect, the surgical instrument 102 and alignment indicator device 104 of the present teachings can be used in combination for accurate anatomical alignment prior to and/or during a surgical procedure. In one aspect, the alignment indicator 104 can be selectively, temporarily coupled to the surgical instrument 102 at one or more steps during a surgical procedure. In another aspect, the alignment indicator 104 can be incorporated into the surgical instrument 102. In one exemplary aspect, the surgical instrument 102 can comprise a resection guide assembly.

Figure 2:
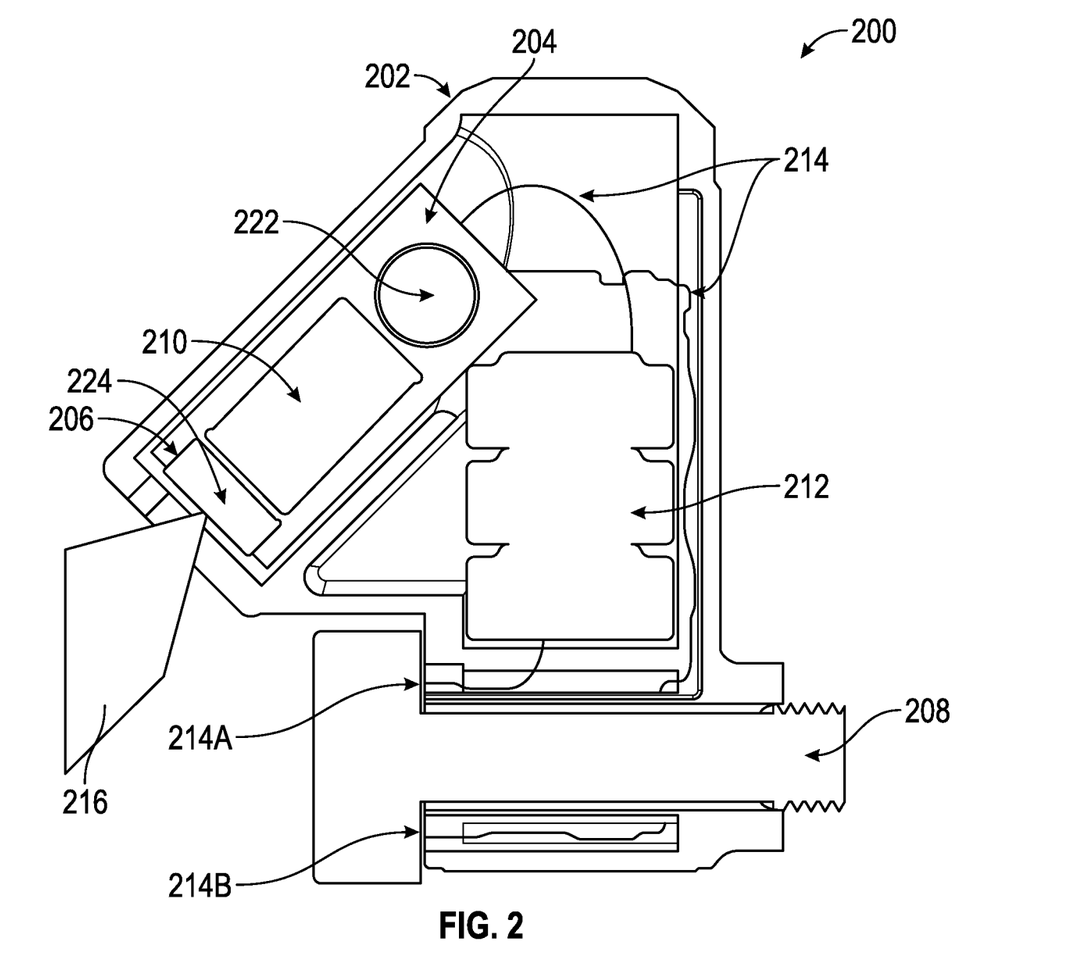
FIG. 2 illustrates one aspect of an alignment indicator device.
Figure 3:
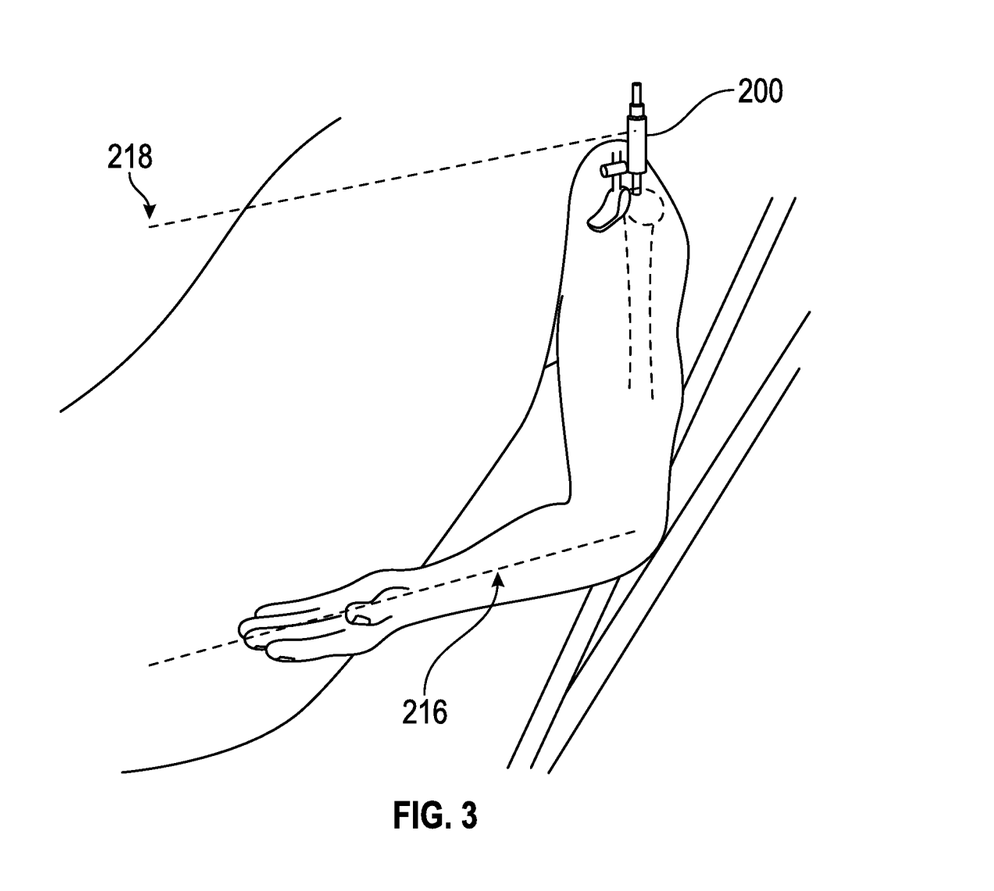
FIG. 3 illustrates another aspect of an alignment indicator device.
Figure 4:
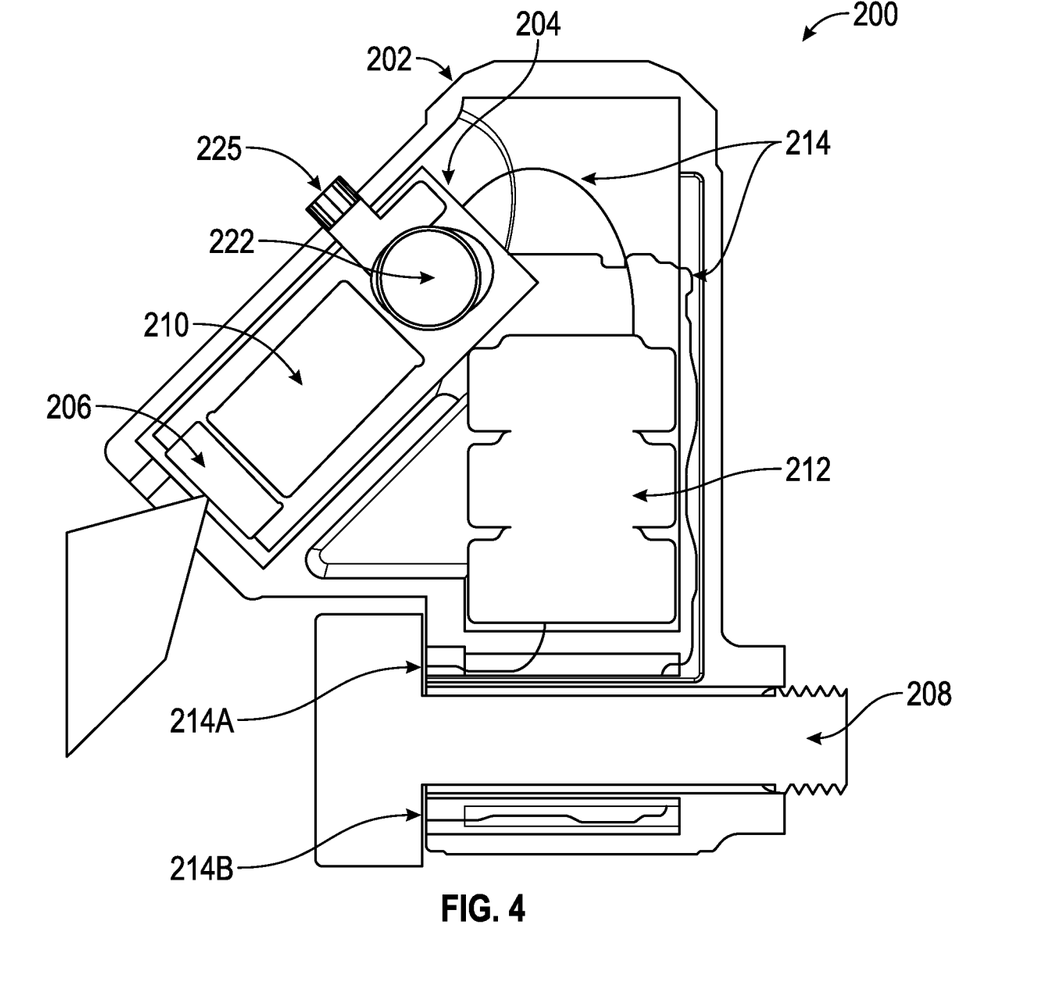
FIG. 4 illustrates another aspect of an alignment indicator device.

In one aspect illustrated in FIGS. 2-4, an alignment indicator device 200 can comprise a housing 202 and at least one light source assembly 204 at least partially disposed in the housing 202. The housing 202 can define an aperture 206. The housing 202 can be selectively securable via a fastener 208 to an instrument 102 in a selected orientation relative to the instrument. The light source assembly 204 can comprise a light source 210 that can be operably coupled to a power source 212 via a power circuit 214. The power source 212 can comprise, for example and without limitation, a battery, a solar cell, a power cord to engage an electrical outlet, and the like. The power circuit 214 can comprise a switch disposed on the exterior surface of the housing or electronic components to enable remote operation of the alignment indicator device 200. The light source 210 can be positioned within the housing 202 to emit through the aperture 206 of the housing 202. Upon activation, the light source assembly 204 can emit a parallax-free alignment indicator 216 along an alignment axis 218. The alignment axis 218 can have at least one of a selected angle $\alpha$ and a selected displacement $\delta$ relative to a selected reference axis. The alignment indicator 216 can comprise, for example and without limitation, light in the form of a line, a dashed line, a dot, a scale, a logo, a geometric shape, and the like. The light source 210 can comprise, for example and without limitation, a laser or a light-emitting diode (LED). The alignment indicator 216 can serve as a guide surgical procedures that require accurate alignment and/or version such as, for example and without limitation, bone resection, implantation of arthroplasty implants, and the like. The alignment indicator 216 can be used to mark the patient's anatomy to facilitate maintenance of alignment or realignment during a procedure.

Figure 5:
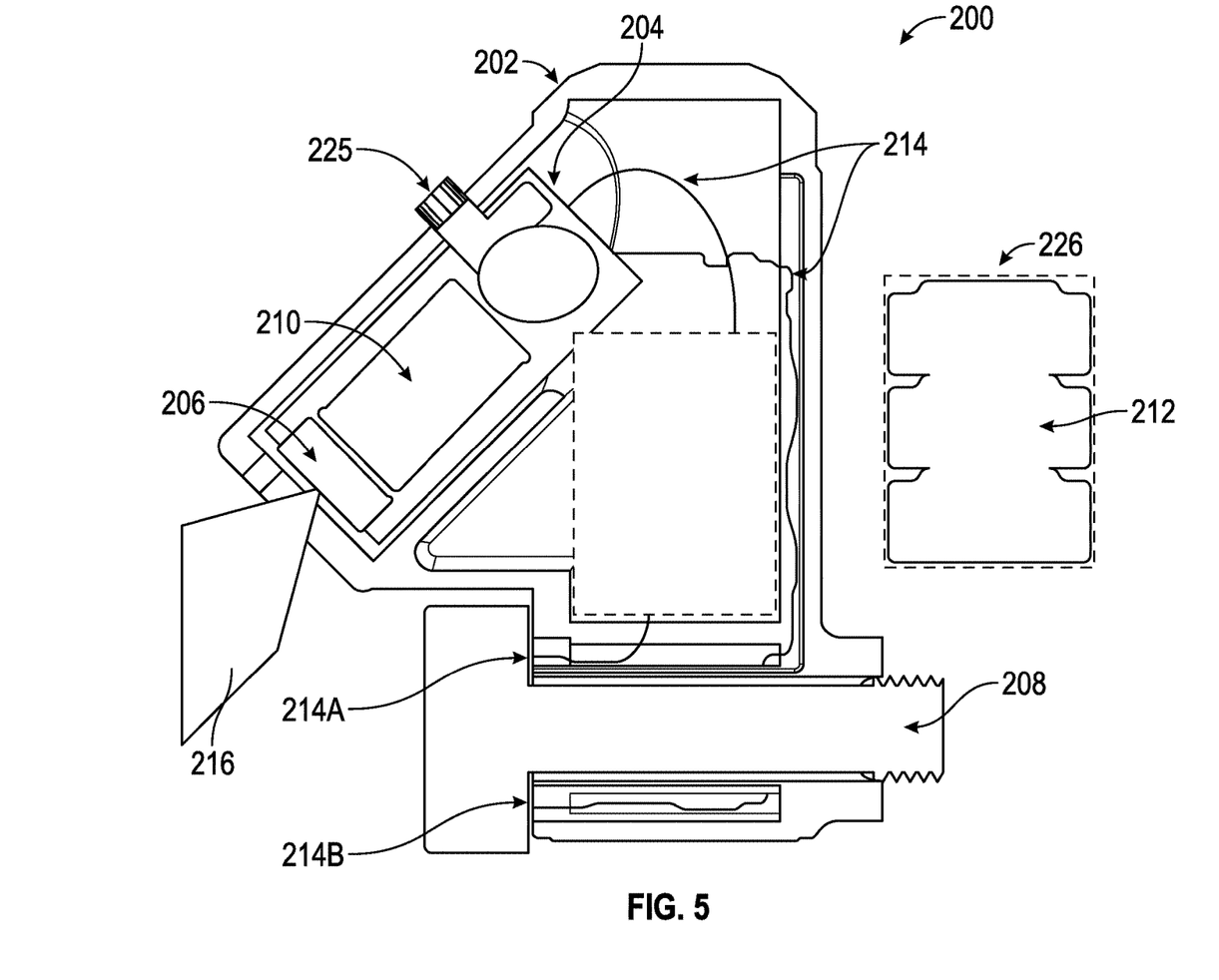
FIG. 5 illustrates another aspect of an alignment indicator device.

In another aspect, the light source assembly 204 can comprise a lens assembly 224 that can selectively adjust the angle and the displacement of the alignment indicator 216 relative to the selected reference axis. The lens assembly 224 can comprise either or both of a mirror and a lens. The lens assembly 224 can further comprise a plurality of either or both of a mirror and a lens. The lens assembly 224 can be fixed or can be adjustable to change one or more of the orientation, intensity, or form of light emitted from the alignment indicator device 200. At least one of a lens and a mirror in the lens assembly 224 can be fixed. In one aspect, the lens assembly 224 (and hence the orientation, intensity, and/or form of light) can be adjusted by a controller 222. In one aspect, lens assembly 224 can be manually adjustable by a user rotating adjuster 225. In another aspect, the controller 222 can have a controller interface operably coupled to the adjuster 224. While FIGS. 4-5 show a manual adjuster 225, it bears emphasis that adjustments to the orientation, intensity, and/or form of light in alignment indicator 216 may occur using all electrical and/or a combination of electrical and mechanical components. The controller 222 can comprise electronic components, servo motors, and circuits that allow for adjustment of the alignment indicator 216 (i.e., the orientation, intensity, and/or form of light). The controller 222 may also allow for remote operation of the controller 222 and remote adjustment of the alignment indicator 216 via either a wired or wireless connection with a computer and controller interface. The controller interface can be on the alignment indicator device 200 or remote thereto, such that the controller 222 can be controlled remotely.

In operation, the adjuster 225 can be adjusted via the controller 222 based on manipulation of the controller interface by a user. The alignment indicator 216 can be adjustable about a continuum of angles with respect to a selected reference axis. Alignment axes about which the alignment indicator 200 can be rotated can include axis 218, 219, and 220. In at least one aspect of the invention, the alignment indicator 200 can be rotated about these axes, as indicated by arrows 218$x$, 219$x$, and 220$x$, to adjust the roll, pitch, and yaw of the alignment indicator 216. Such rotation can occur manually using adjuster 225 and/or using electronic components, servo motors, and circuits in the controller 222. In other words, in at least one aspect, a light beam, represented by alignment indicator 216, can be rotated about at least three axes to adjust the roll, pitch, and/or yaw of the light beam. This can be accomplished by rotating external components of the alignment indicator device 200, such as housing 202 or light source assembly 204, or by adjusting internal components, such as lenses and mirrors, as explained above. The alignment indicator 216 can be continuously adjustable or can be adjustable in fixed increments about one or more of the alignment axes.

In another aspect, the orientation of the alignment indicator 216 can be an output of the controller operably coupled to the adjuster. More specifically, the orientation, or humeral version, can be output in a numerical format on a display or by projecting a number as part of, or separate from, the alignment indicator 216 using light source 210. If a numerical representation of the humeral version is output on a display, the display can be located on the adjustment indicator device 200 itself (e.g., on housing 202 or as part of controller 222), or remote to the alignment indicator device (e.g., on a computer that controls the controller 222).

In one exemplary aspect, details of a specific surgery or patient may be uploaded to a computer and the controller 222 to thereby input a desired humeral version to the system. The desired humeral version may be patient-specific in that the humeral version depends on a particular patient's anatomy for a particular surgical procedure. Additionally or alternatively, the desired humeral version may be doctor-specific, in that a particular doctor may prefer a particular orientation of the humerus relative to other anatomy when performing a particular surgical procedure. In such cases, controller 222 may receive the input humeral version from the computer and adjust the alignment indicator to the proper orientation. Displaying the humeral version on a display would aid in ensuring that the desired humeral version has been achieved.

In another aspect, the alignment indicator device 200 can further comprise a plurality of alignment indicators 216. Each of the plurality of alignment indicators 216 can be projected along an axis relative to a unique selected reference axis. In another aspect, each of the plurality of alignment indicators 216 can be projected along an axis having a unique selected angle relative to the selected reference axis. Additionally or alternatively, each of the plurality of alignment indicators 216 can be spaced along the alignment axis. Such a plurality of alignment indicators 216 can be useful to provide a surgeon with options or can be useful in order to index the procedure or additional procedures relative to additional anatomical sites, surgical instruments, or implants. In one exemplary aspect, when performing an elbow, wrist, hand, or glenoid procedure concurrently with a shoulder replacement procedure, the alignment indicator device 200 can be used to align or orient multiple anatomical features. In another exemplary aspect, an alignment indicator 216 or one of a plurality of alignment indicators 216 can be used to compare and adjust limb length across the midline of the body using the opposite limb, e.g., using the anatomical characteristics of the right arm to align the anatomical characteristics of the left arm. In another aspect, the alignment indicator device 200 can have multiple alignment indicator settings or modes (or visual variations on a single alignment indicator setting) and can comprise a switch or setting to modulate or toggle between the settings. In yet another aspect, the alignment indicator device 200 can comprise a control to change the appearance of the alignment indicator 216.

In another aspect, the fastener 208 of the housing 202 can comprise, for example and without limitation, a magnet, a threaded member, a clip, and the like. The fastener 208 can further comprise a vibration dampener. The vibration dampener can comprise a spring. In another aspect, fastener 208 may comprise a servo motor fastened to instrument 102 and which allows alignment indicator device 200 to rotate about one or more alignment axes.

In another aspect, the alignment indicator device 200 can comprise a power circuit 214 that can have a first lead 214A and a second lead 214B (see FIGS. 2 and 4), both exposed on an exterior surface of the housing 202 designed to contact a metal object to complete the power circuit 214 and activate the light source 210. In one aspect, the metal object can comprise a portion of the instrument 102. In another aspect, the metal object can comprise a portion of the fastener 208 of the housing 202. In yet another aspect, the metal object can comprise another device or instrument proximate the patient. In yet another aspect, the first lead 214A and the second lead 214B of the power circuit 214 can be inside the housing and the power circuit 214 can be completed upon, e.g., application of pressure to a pressure switch or via pressure when the alignment indicator device 200 is secured to another object.

In another aspect illustrated in FIG. 5, at least a portion of the light source assembly 204 can comprise an interchangeable cartridge 226 that can be receivable within the housing 202. The modular cartridge 226 can be used in a plurality of either disposable or reusable housings 202 in order to increase intraoperative flexibility. In one aspect, at least one of the housing 202 or modular cartridge 226 can comprise a power source 212 that can be rechargeable. In an additional or alternative aspect, modular cartridge 226 can contain information specific to a patient or a specific surgery, such as settings for either or both of the light source assembly 204 and the controller 222. In one aspect, such information can be contained on a memory card.

Figure 6:
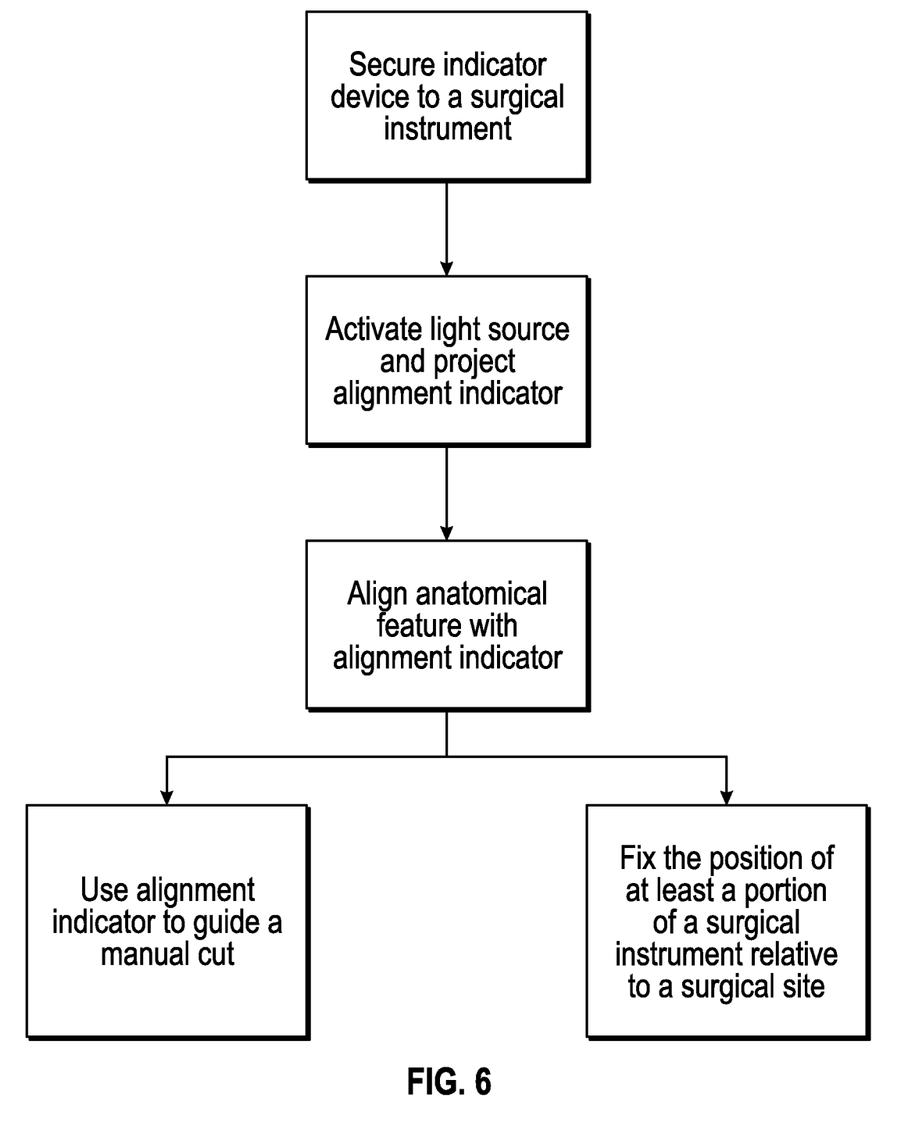
FIG. 6 is a flow chart illustrating an exemplary process of anatomical registration of an alignment indicator device to a surgical site.

In other aspects illustrated in FIG. 6, the present teachings provide for methods for accurately determining anatomical orientation and, additionally or alternatively, maintaining or recreating anatomical orientation prior to and/or during a surgical procedure. Such methods can comprise securing a parallax-free alignment indicator device 200 to a surgical instrument, activating a light source 210 of the device 200 to project an alignment indicator 216 (e.g., laser light or LED light) along an alignment axis, aligning either or both of another surgical instrument and an anatomical feature of a patient with the alignment indicator 216, and either or both of using the alignment indicator 216 to guide a manual cut and fixing the position of at least a portion of the surgical instrument 102 relative to a surgical site on the patient. The method can further comprise providing a mark on the patient along the alignment indicator 216. In one aspect, the surgical instrument can be a cut guide assembly. In another aspect, the surgical site can be a proximal humerus. In another aspect, the anatomical feature of the patient can comprise a forearm.

In one exemplary aspect, a method for facilitating a shoulder replacement procedure can comprise placing a cut guide assembly on a reamer in a proximal humerus of a patient, securing a parallax-free alignment indicator device 200 to the cut guide assembly, activating the light source 210 of the device 200 to project an alignment indicator 216 along the version axis, aligning a forearm of a patient with the alignment indicator 216, fixing the position of at least a portion of the cut guide assembly relative to the proximal humerus, and cutting the proximal humerus according to the cut guide assembly. The method can also comprise using the alignment indicator 216 to ensure the version of a subsequent rasp or reamer inserted into the cut humerus is aligned with the version of the humeral cut. The method can also comprise using the alignment indicator 216 to ensure the version of an implant is aligned with both the version of the rasp and the version of the cut humerus prior to engagement with the cut humerus.

Some numbered examples of the present subject matter are listed below:

Example 1 is a device that can comprise a housing defining an aperture, wherein the housing can be selectively securable via a fastener to an instrument in a selected orientation relative to the instrument; and a light source assembly that can be at least partially disposed in the housing, the light source assembly comprising a light source operably coupled to a power source via a power circuit, wherein the light source can be positioned within the housing to emit through the aperture of the housing, wherein, upon activation, the light source assembly can emit a parallax-free alignment indicator along an alignment axis having at least one of a selected angle and a selected displacement relative to a selected reference axis, and wherein the alignment indicator can guide a surgical procedure.

In Example 2, the subject matter of Example 1 can optionally be configured such that the light source assembly comprises one of a laser and a light-emitting diode.

In Example 3, the subject matter of any one or more of Examples 1-2 can optionally be configured such that the light source assembly further comprises an adjuster for selectively adjusting at least one of the selected angle and the selected displacement of the alignment indicator.

In Example 4, the subject matter of Example 3 can optionally be configured such that the adjuster comprises a mirror.

In Example 5, the subject matter of any one or more of Examples 3-4 can optionally be configured such that the adjuster comprises a lens.

In Example 6, the subject matter of any one or more of Examples 3-5 can optionally be configured such that the adjuster can be manually adjustable by a user.

In Example 7, the subject matter of any one or more of Examples 3-6 can further comprise a controller having a controller interface, wherein the controller can be operably coupled to the adjuster, wherein the adjuster can be adjustable via the controller based on manipulation of the controller interface by a user.

In Example 8, the subject matter of any one or more of Examples 1-7 can optionally be configured such that the alignment indicator further comprises a plurality of alignment indicators, wherein each of the plurality of alignment indicators can be projected along an alignment axis having a unique selected angle relative to the selected reference axis.

In Example 9, the subject matter of any one or more of Examples 1-8 can optionally be configured such that the alignment indicator further comprises a plurality of alignment indicators, wherein each of the plurality of alignment indicators can be spaced along the alignment axis.

In Example 10, the subject matter of any one or more of Examples 1-9 can optionally be configured such that the alignment indicator comprises at least one of a line, a dot, a scale, and a logo.

In Example 11, the subject matter of any one or more of Examples 1-10 can optionally be configured such that the alignment axis can be adjustable about and between a first angle and a second angle with respect to the selected reference axis.

In Example 12, the subject matter of Example 11 can optionally be configured such that the alignment axis can be adjustable in fixed increments.

In Example 13, the subject matter of any one or more of Examples 1-12 can optionally be configured such that the power source comprises one of a battery and a solar cell.

In Example 14, the subject matter of any one or more of Examples 1-13 can optionally be configured such that the power circuit comprises a first lead and a second lead, both exposed on an exterior surface of the housing in a location designed to contact a metal object to complete the power circuit and activate the light source.

In Example 15, the subject matter of Example 14 can optionally be configured such that the metal object comprises one of a portion of the instrument and a portion of the fastener of the housing.

In Example 16, the subject matter of any one or more of Examples 1-15 can optionally be configured such that the power circuit comprises a first lead and a second lead that can be selectively coupled to complete the power circuit upon application of pressure.

In Example 17, the subject matter of any one or more of Examples 1-16 can optionally be configured such that the power circuit comprises a switch disposed on an exterior surface of the housing.

In Example 18, the subject matter of any one or more of Examples 1-17 can optionally be configured such that the fastener comprises one of a magnet, a threaded member, and a clip.

In Example 19, the subject matter of any one or more of Examples 1-18 can optionally be configured such that the fastener further comprises a vibration dampener.

In Example 20, the subject matter of Example 19 can optionally be configured such that the vibration dampener comprises a spring.

In Example 21, the subject matter of any one or more of Examples 1-20 can optionally be configured such that at least a portion of the light source assembly comprises a modular cartridge receivable in the housing.

Example 22 is a method the can comprise securing a device to a surgical instrument, the device comprising: a housing defining an aperture, wherein the housing can be selectively securable via a fastener to the surgical instrument in a selected orientation relative to the instrument; and a light source assembly at least partially disposed in the housing, the light source assembly comprising a light source operably coupled to a power source via a power circuit, wherein the light source can be positioned within the housing to emit through the aperture of the housing; activating the light source to project a parallax-free alignment indicator along an alignment axis having at least one of a selected angle and a selected displacement relative to a selected reference axis; aligning an anatomical feature of a patient with the alignment indicator; fixing the position of at least a portion of the surgical instrument relative to a surgical site on the patient.

In Example 23, the subject matter of Example 22 can optionally be configured such that the surgical instrument can be a cut guide assembly.

In Example 24, the subject matter of any one or more of Examples 22-23 can optionally be configured such that the surgical site comprises the proximal humerus.

In Example 25, the subject matter of any one or more of Examples 22-24 can optionally be configured such that the anatomical feature of the patient comprises a forearm.

In Example 26, the subject matter of any one or more of Examples 22-25 optionally includes providing a mark on the patient along the alignment indicator.

Example 27 is a method that can comprise placing a cut guide assembly on a first rasp engaged in a proximal humerus of a patient; securing a device to the cut guide assembly, the device comprising: a housing defining an aperture, wherein the housing can be selectively securable via a fastener to the surgical instrument in a selected orientation relative to the instrument; and a light source assembly comprising a light source operably coupled to a power source via a power circuit, wherein the light source can be in communication with the aperture of the housing; activating the light source to project a parallax-free alignment indicator along an alignment axis having at least one of a selected angle and a selected displacement relative to a selected reference axis; aligning a forearm of a patient with the version indicator; fixing the position of at least a portion of the cut guide assembly relative to the proximal humerus; cutting the proximal humerus according to the cut guide assembly.

In Example 28, the subject matter of Example 27 optionally includes using the version indicator to ensure the version of a second rasp inserted into the cut humerus is aligned with the version of the humeral cut.

In Example 29, the subject matter of Example 28 optionally includes using the version indicator to ensure the version of an implant is aligned with both the version of the second rasp and the version of the cut humerus prior to engagement with the cut humerus.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b) at the time of filing this application, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device, comprising:
   a housing defining an aperture;
   a fastener, wherein the housing is selectively securable via the fastener to an instrument in a selected orientation relative to the instrument; and
   a light source assembly at least partially disposed in the housing, the light source assembly comprising:
   a light source operably coupled to a power source via a power circuit, wherein the light source comprises a laser or a light-emitting diode and is positioned within the housing to emit light through the aperture of the housing, wherein, upon activation, the light source assembly emits a parallax-free alignment indicator along an alignment axis having at least one of a selected angle or a selected displacement relative to a selected reference axis, wherein the alignment indicator is configured to be rotatable about at least three alignment axes to adjust a roll, a pitch, and a yaw of the alignment indicator, and wherein the alignment indicator is configured to guide a surgical procedure; and
   an adjuster for selectively adjusting at least one of the selected angle or the selected displacement of the alignment indicator;
   wherein the adjuster comprises at least one of a mirror or a lens;
   wherein the alignment axis is adjustable in fixed increments about and between a first angle and a second angle with respect to the selected reference axis;
   wherein the power circuit comprises a first lead and a second lead, both exposed on an exterior surface of the housing in a location designed to contact a metal object to complete the power circuit and activate the light source; and
   wherein the metal object comprises a portion of the fastener.

2. The device of claim 1, wherein the adjuster is manually adjustable by a user.

3. The device of claim 1, further comprising a controller having a controller interface, wherein the controller is operably coupled to the adjuster, wherein the adjuster is adjustable via the controller based on manipulation of the controller interface by a user.

4. The device of claim 1, wherein the alignment indicator further comprises a plurality of alignment indicators, wherein each of the plurality of alignment indicators is projected along an alignment axis having a unique selected angle relative to the selected reference axis.

5. The device of claim 1, wherein the alignment indicator comprises at least one of a line, a dot, a scale, or a logo.

6. The device of claim 1, wherein the power source comprises a battery or a solar cell.

7. The device of claim 1, wherein the first lead and the second lead are selectively coupled to complete the power circuit upon application of pressure.

8. The device of claim 1, wherein the power circuit comprises a switch disposed on an exterior surface of the housing.

9. The device of claim 1, wherein the fastener comprises a threaded member.

10. A method, comprising:
    placing an orthopedic bone cut guide on a reamer in a proximal humerus of a patient;
    securing an alignment indicator device to the bone cut guide, the alignment indicator device comprising:
       a housing defining an aperture, wherein the housing is selectively securable via a fastener to the bone cut guide in a selected orientation relative to the bone cut guide; and
       a light source assembly at least partially disposed in the housing, the light source assembly comprising a light source operably coupled to a power source via a power circuit, wherein the light source is positioned within the housing to emit through the aperture of the housing;
    activating the light source to project a parallax-free alignment indicator along an alignment axis, wherein the alignment indicator is rotatable about at least three axes to adjust a roll, a pitch, and a yaw of the alignment indicator;
    aligning an anatomical feature of a patient with the alignment indicator; and
    fixing the position of at least a portion of the bone cut guide relative to a surgical site on the patient.

* * * * *